United States Patent
Welker et al.

(10) Patent No.: US 6,743,998 B2
(45) Date of Patent: *Jun. 1, 2004

(54) METHOD AND APPARATUS FOR INSPECTION OF HOT GLASS CONTAINERS

(75) Inventors: Mathias P. Welker, Toledo, OH (US); D. Wayne Leidy, Perrysburg, OH (US); Matthew D. Redd, Toledo, OH (US)

(73) Assignee: Owens-Brockway Glass Container Inc., Toledo, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 10/373,548

(22) Filed: Feb. 24, 2003

(65) Prior Publication Data

US 2003/0155281 A1 Aug. 21, 2003

Related U.S. Application Data

(63) Continuation of application No. 09/495,271, filed on Jan. 31, 2000, now Pat. No. 6,639,166.

(51) Int. Cl.[7] ................................. B07C 5/00
(52) U.S. Cl. ................. 209/524; 209/587; 250/223 B; 65/29.12; 65/158
(58) Field of Search ......................... 289/522, 523, 289/524, 587, 588, 938; 198/341, 445; 250/223 B, 224; 65/29.12, 158, 160, 163

(56) References Cited

U.S. PATENT DOCUMENTS

| | | |
|---|---|---|
| 3,968,368 A | 7/1976 | Sager |
| 4,331,227 A | 5/1982 | Risley |
| 4,421,542 A | 12/1983 | Poad et al. |
| 4,427,431 A | 1/1984 | Mumford et al. |
| 4,494,656 A | 1/1985 | Shay et al. |
| 4,548,633 A | 10/1985 | Nebelung |
| 4,574,009 A | 3/1986 | Welker |
| 5,279,636 A | 1/1994 | Waters |
| 5,296,707 A | 3/1994 | Nozu |
| 5,437,702 A | 8/1995 | Burns et al. |
| 5,734,702 A | 3/1998 | Sugimura |
| 5,897,677 A | 4/1999 | Flynn |

FOREIGN PATENT DOCUMENTS

| | | |
|---|---|---|
| EP | 607558 | 7/1994 |
| FR | 2 760 528 | 5/1997 |

*Primary Examiner*—Donald P. Walsh
*Assistant Examiner*—Kaitlin S Joerger

(57) ABSTRACT

An opposed pair of inwardly facing radiant energy detecting sensors (20, 22) is positioned to sight on freshly formed glass containers (C) being conveyed on a side by side pair of conveyors (12, 14) to determine if any of the containers is misoriented from its desired orientation. Each sensor has a sharply focused fiber and lens assembly (24) that is focused to sense radiant energy in a cone of view no greater than 1°. A baffle (32) is positioned between the conveyors and in alignment with the opposed sensors, to isolate the sensors from radiant energy emitted by containers on the away conveyor.

11 Claims, 3 Drawing Sheets

METHOD AND APPARATUS FOR INSPECTION OF HOT GLASS CONTAINERS

CROSS REFERENCE TO RELATED APPLICATION

This application is a continuation of application Ser. No. 09/495,271, which was filed on Jan. 31, 2002. now U.S. Pat. No. 6,639,166

BACKGROUND OF THE INVENTION

1. Field of the Invention

This invention relates to a method of, and apparatus for, inspecting hot, freshly formed glass containers as they travel, in sequence, to a processing or other treatment station.

2. Description of the Prior Art

As is taught, for example, in U.S. Pat. No. 3,968,368 (Sager), which was assigned to a predecessor of the assignee of the present invention and the disclosure of which is incorporated by reference herein, it is important to inspect freshly formed glass containers, while they still possess considerable latent heat from their manufacture, to eliminate containers that are out of specification in any of several ways, such as by having two bottles stuck together, or are out of position on a container transfer conveyor, such as by being "down" on their sides. The aforesaid '368 patent proposed to accomplish such inspection by sensing radiant heat emitted by the bottles as they passed, in sequence, past radiation sensing probes. However, the probes used in the apparatus of the '368 patent did not adequately focus the emitted radiation, and required too many time-consuming adjustments to permit them to be employed on a regular basis in a high production glass container manufacturing plant.

The problem of detecting out of orientation conditions in a procession of freshly formed glass containers is also addressed in U.S. Pat. No. 4,494,656 (Shay et al.), which teaches the use of radiant energy directed toward the containers, for example, from a laser, and sensing the presence or absence of such radiant energy in relation to the presence or absence that would be experienced if the containers were properly oriented, as a way of detecting a misoriented condition of any of the containers. However, the equipment needed to practice the teachings of the '656 patent is expensive, and it cannot be readily adapted to the inspection of containers being conveyed on dual, side by side conveyors from a single forming machine, an arrangement that is characteristic of modern, high production glass forming machines, because of the need to arrange the laser radiation devices facing inwardly, toward one another, which can lead to interference between the sensed signals of oppositely facing lasers.

SUMMARY OF THE INVENTION

The aforesaid and other problems associated with the inspection of freshly formed glass containers are overcome by the method and apparatus of the present invention, in which radiant energy emitted by the containers, because of the latent heat they still possess from the manufacturing process, is sensed by an optical, focused sensor as the bottles are conveyed in sequence past the sensor, or past a multiplicity of like sensors that inspect the containers for various out of specification or out of orientation conditions. The arrangement of the invention is easily adapted to a dual conveyor system because the sensors are positioned externally of the conveyors and face inwardly, requiring only a baffle or radiation shield between the conveyors to prevent a sensor from sensing the condition of a container on the away conveyor rather than the near conveyor.

Accordingly, it is an object of the present invention to provide an improved method of, and apparatus for, inspecting hot, freshly formed glass containers, as the containers move in sequence toward a processing station, for an out of orientation or out of specification condition. More particularly, it is an object of the present invention to provide a method and apparatus as described above that is readily adaptable to the inspection of containers being conveyed on dual, side by side conveyors.

For a further understanding of the present invention and the objects thereof, attention is directed to the drawing and the following brief description thereof, to the detailed description of the preferred embodiment and to the appended claims.

DETAILED DESCRIPTION OF THE PREFERRED EMBODIMENT

Figure 1:
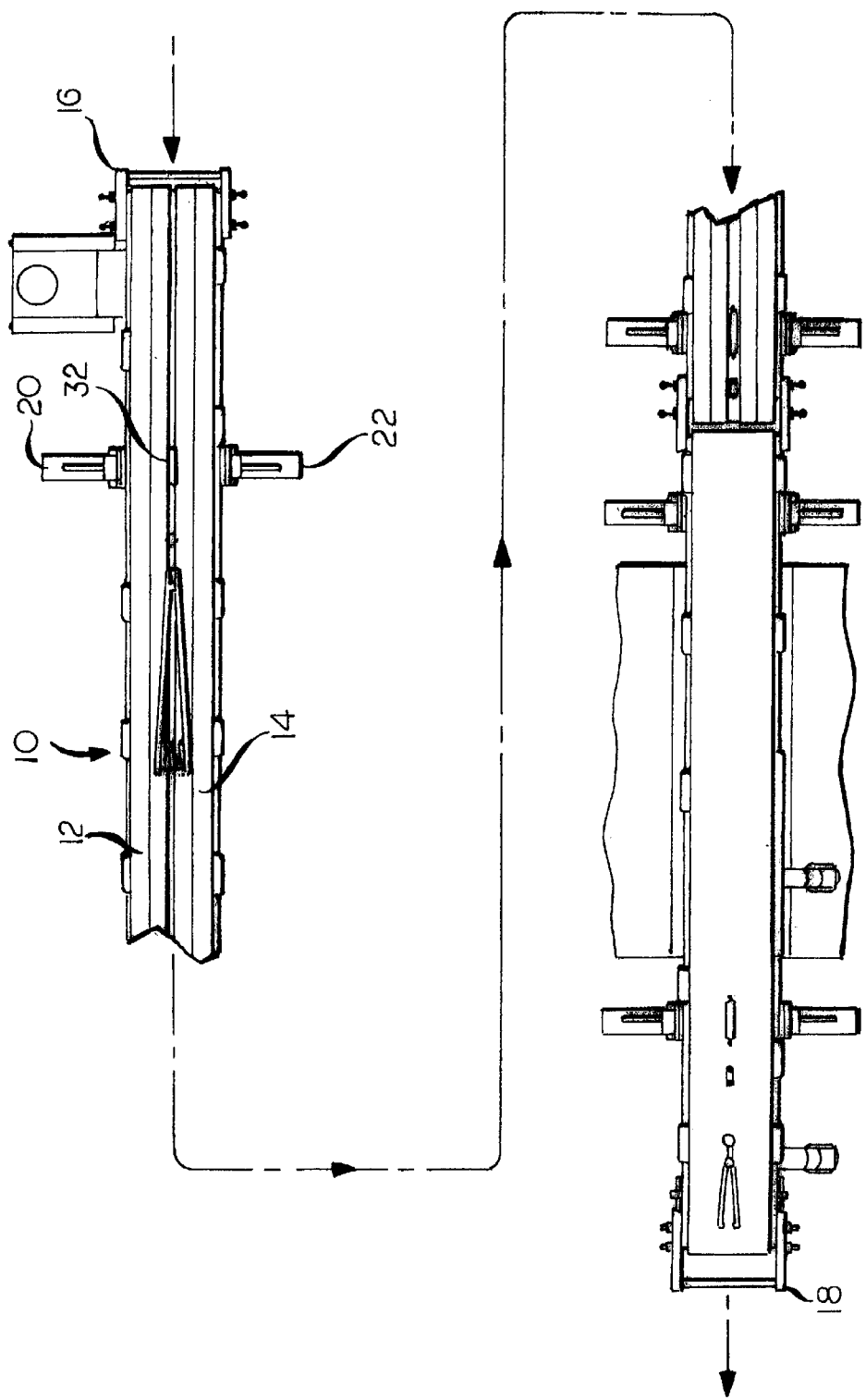
FIG. 1 is a plan view of dual conveyor apparatus for conveying freshly formed glass containers from an inlet to the conveyor to an outlet from the conveyor, the apparatus incorporating radiation sensors according to the preferred embodiment of the present invention for sensing thermal radiation from the containers.

FIG. 1 illustrates a conveyor assembly, indicated generally by reference numeral 10, which is made up of side by side conveyors 12, 14. The conveyor assembly 10 is used to convey, in sequence, a plurality of freshly formed glass containers from an inlet end 16, which is positioned to receive containers from a glass container forming machine of the individual section (I.S.) type, not shown, to an outlet end 18, which is positioned to discharge the containers to a cross-conveyor, not shown, which delivers the containers to a lehr loader for transfer into an annealing lehr. This arrangement is generally shown and described, for a single conveyor conveyor assembly, in published European Patent Application EP 0 949 211 A2, which corresponds to U.S. patent application Ser. No. 09/055/512, now U.S. Pat. No. 6,076,654 (Leidy), an application that is assigned to the assignee of this application, the disclosure of which is incorporated by reference herein.

As the containers are carried along by the conveyors 12, 14 to the outlet end 18 of the conveyor assembly 10, they pass by one or more opposed pairs of inwardly facing sensors, such as the sensors 20, 22. The sensors 20, 22 are positioned to detect thermal radiation emitted by the containers, which will be substantial due to the residual latent heat in the containers as a result of their recent manufacture by an I.S. machine.

Figure 2:
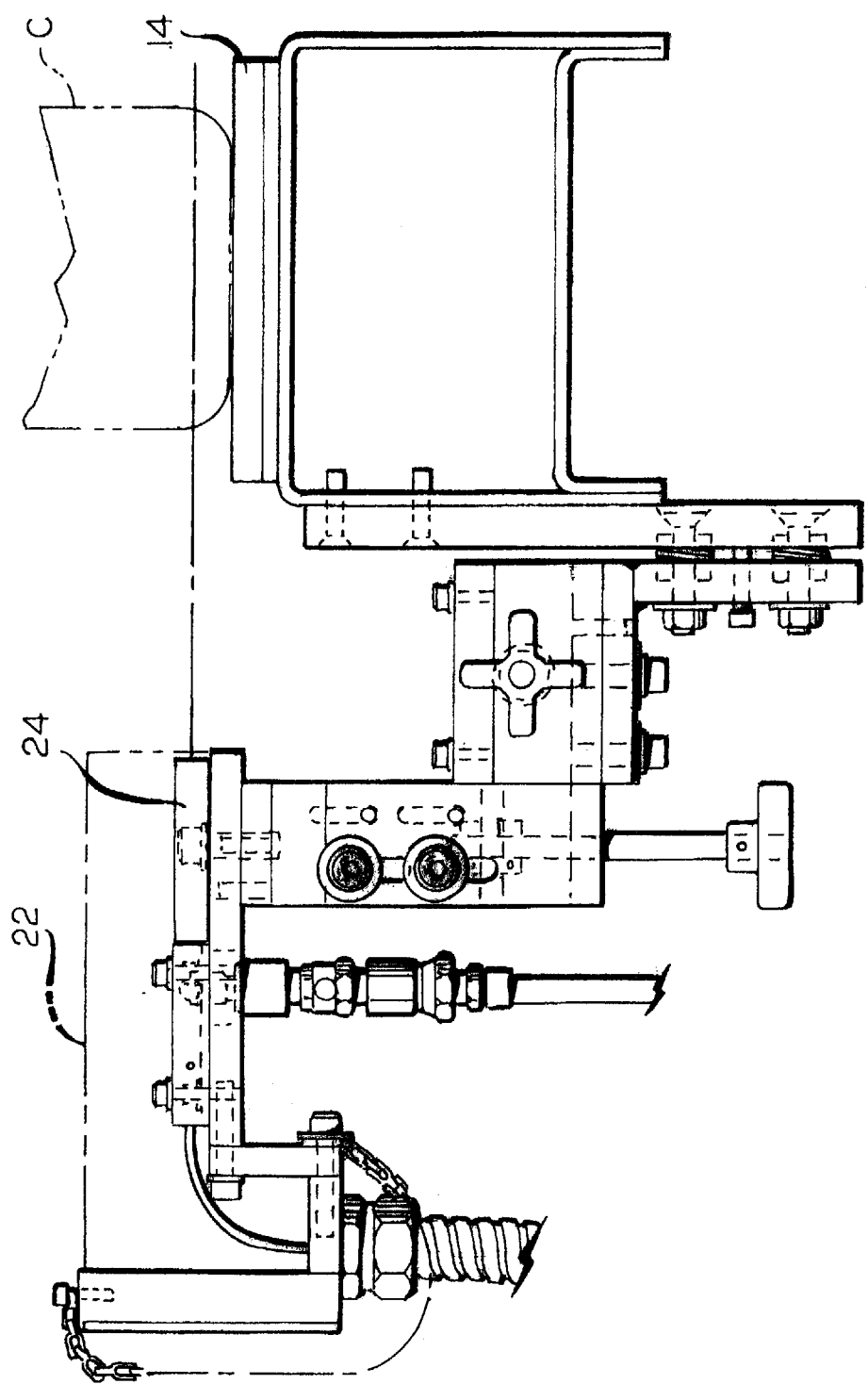
FIG. 2 is a fragmentary elevational view, at an enlarged scale, of one of the sensors of the apparatus of FIG. 1.
Figure 3:
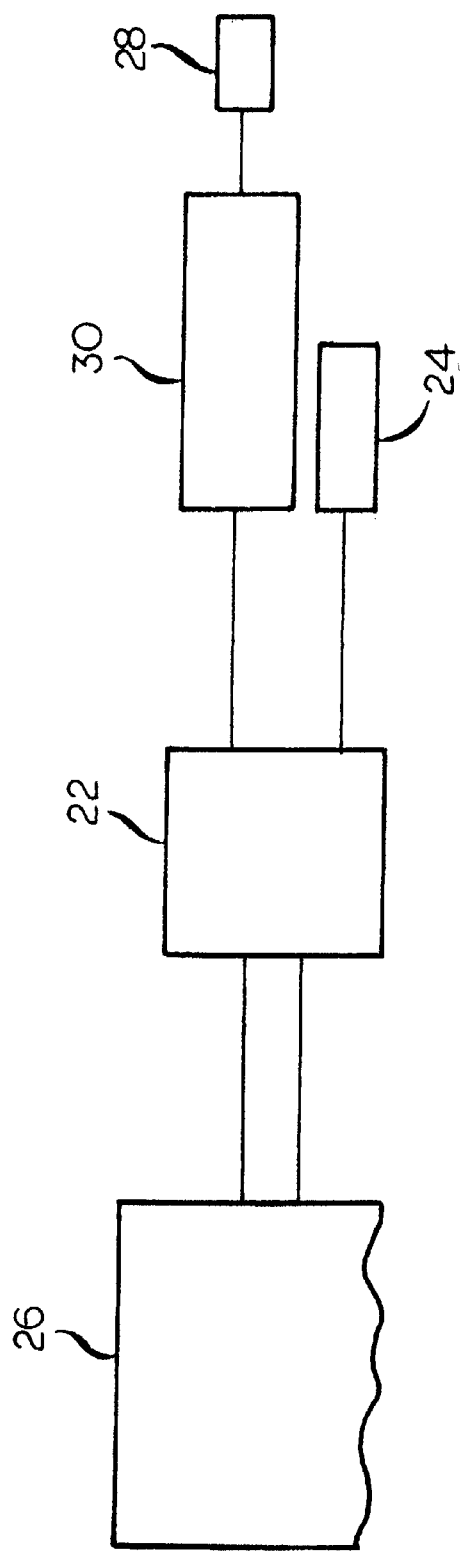
FIG. 3 is a fragmentary schematic view of a control system for controlling the operation of one of the sensors of FIGS. 1 and 2.

As is shown in FIG. 2, the sensor 22, and all like sensors, incorporates a fiber and lens assembly 24 that receives sharply focused thermal radiant energy from a container C, shown fragmentarily and in broken line, that is being conveyed past the sensor 22 by the conveyor 14. As shown in FIG. 3, a signal indicative of the presence or absence of detected radiant energy is transmitted to a detector/controller 26, which serves to actuate, through a J box 30, a solenoid 28 of a blow off device, not shown, when the pattern and timing of radiant energy received by the sensor 22 does not correspond to the pattern that is expected when the container C is in its desired position and orientation. For example, the sensor 22 will sense a "down" condition of the container C or a jammed condition of a multitude of such containers, if such a condition is present and will cause the container C, together with any other misoriented containers C, to be discharged before any such containers C reaches the outlet end 18 of the conveyor assembly 10. The detector/controller 26 communicated with a display station 34. Configuration parameters and other data are communicated to and from the display station 34 and the detector/controller 26.

Requirements for the fiber and lens assembly 24 of the sensor 22 are met in a satisfactory manner by an infrared edge detector/sensor assembly of the type available from Mikron Instrument Co. Inc. of Oakland, N.J. under their designation 17528-CD, an assembly that includes a detector unit under their designation 17516-1 and a fiber optic, lens and air purge assembly under their designation 17517-1, for transmitting a sensed analog signal to the detector/controller 26. Such a sensor assembly is capable of detecting energy in a cone of view no greater than 1°. As is clear from FIG. 2, the fiber and lens assembly 24 of the sensor 22 is positioned to sight on a portion of the container C that is just slightly above the conveyor 14, so that it is sighting on a rounded heel portion of the container C. As such, the pattern of radiant energy detected by the assembly 24 will be quite different, for example, if the container C is in a down condition than it will be if the container C is in its proper upright condition.

In a dual conveyor system, such as that illustrated in FIG. 1, it is preferable to isolate the effects of the radiant energy by containers on each conveyor to sensors associated only with that conveyor. This is done, for example, by positioning a baffle 32, preferably an insulated or internally cooled baffle, between aligned and opposed sensors 20, 22, so that the sensor 20 only senses the condition of containers C on the conveyor 12, and the sensor 22 only senses the condition of containers C on the conveyor 14.

In the operation of an inspection system according to this invention, it is contemplated that the desired signal to be received by each sensor can be varied in real time as a function of forming machine speed, to thereby eliminate the need to recalibrate the system for machine speed variations, and it is contemplated that this can be done in increments as small as 1/16 of a machine degree. It is also contemplated, based on the accuracy of the system, that it can be adapted to automatically count the containers being inspected.

Although the best mode contemplated by the inventors for carrying out the present invention as of the filing date hereof has been shown and described herein, it will be apparent to those skilled in the art that suitable modifications, variations and equivalents may be made without departing from the scope of the invention, such scope being limited solely by the terms of the following claims and the legal equivalents thereof.

What is claimed is:

1. Apparatus for inspecting hot, freshly formed glass containers, said apparatus comprising:

a conveyor for conveying hot, freshly formed containers past an inspection station; and a radiant energy detecting sensor positioned at the inspection station for receiving thermal energy emitted by the containers, the radiant energy detecting sensor being focused to sense thermal energy in a small cone of view.

2. Apparatus according to claim 1 wherein said sensor is positioned, relative to said conveyor, to receive thermal energy from a position of a container on the conveyor that is slightly above a rounded heel portion of the container when the container is in its proper upright condition.

3. Apparatus according to claim 1 wherein the radiant energy detecting sensor is focused to sense thermal energy in a cone of view no greater than 1°.

4. Apparatus for inspecting hot, freshly formed glass containers, said apparatus comprising:

a first conveyor for conveying hot, freshly formed containers past a first inspection station;

a second conveyor for conveying hot, freshly formed containers past a second inspection station;

a first radiant energy detecting sensor positioned at the first inspection station for receiving thermal energy emitted by the containers on the first conveyor, the first radiant energy detecting sensor being focused to sense thermal energy in a small cone of view;

a second radiant energy detecting sensor positioned at the second inspection station for receiving thermal energy emitted by the containers on the second conveyor, the second radiant energy detecting sensor being focused to sense thermal energy in a small cone of view;

said first and second radiant energy detecting sensors being opposed to one another and situated externally of both said first conveyor and said conveyor; and a baffle positioned between said first conveyor and said second conveyor and aligned with said first radiant energy detecting sensor and said second radiant energy detecting sensor for preventing said first radiant energy detecting sensor from receiving radiant energy from containers on said second conveyor and for preventing said second radiant energy detecting sensors from receiving radiant energy from containers on said first conveyor.

5. Apparatus according to claim 4 wherein:

said first radiant energy detecting sensor is positioned relative to said first conveyor, to receive thermal energy from a position of a container on the first conveyor that is slightly above a rounded heel portion of the container on the first conveyor when the container on the first conveyor is in its proper upright condition; and said second radiant energy detecting sensor is positioned, relative to said second conveyor, to receive thermal energy from a position of a container on the second conveyor that is slightly above a rounded heel portion of the container on the second conveyor when the container on the second conveyor is in its proper upright condition.

6. The method of detecting a misoriented condition of a container in a supply of hot, freshly formed glass containers, the method comprising:

moving the supply of containers past an inspection station;

providing a radiant energy detecting sensor at the inspection station, the radiant energy detecting sensor being focused to sense thermal energy in the containers in a small cone of view;

sensing, by the radiant energy detecting sensor, radiant energy from each container in the supply of containers moving past the inspection station; and activating a solenoid to reject a container when the radiant energy detected therefrom does not correspond to the radiant energy that would be sensed from a properly oriented container.

7. The method according to claim 6 wherein the radiant energy detecting sensor senses radiant energy from a position of each container that is slightly above a rounded heel portion of the container when the container is in its proper upright orientation.

8. The method of detecting a misorientated condition of a container in a supply of hot, freshly formed glass containers, the method comprising:

provides moving a first portion of the supply of containers past a first inspection station;

moving a second portion of the supply of containers past a second inspection station;

providing a first radiant energy detecting sensor at the first inspection station, the first radiant energy detecting sensor being focused to sense thermal energy in a small cone view;

providing a second radiant energy detecting sensor at the second inspection station, the second radiant energy detecting sensor being focused to sense thermal energy in a small cone of view;

sensing, by the first radiant energy detecting sensor, radiant energy from each container in the first portion of the supply of containers moving past the first inspection station;

sensing, by the second radiant energy detecting sensor, radiant energy from each container in the second portion of the supply of containers moving past the second inspection station; and actuating a solenoid associated with the first energy detecting sensor to reject a container on the first conveyor when the radiant energy detected therefrom does not correspond to the radiant energy that would be sensed from a properly oriented container on the first conveyor.

9. The method according to claim 8 and further comprising:

isolating the second portion of the supply of containers moving past the second inspection station from transmitting radiant energy to the first radiant energy detecting sensor, to prevent the containers in the first portion of the supply of containers moving past the first inspection station from transmitting radiant energy to the second radiant energy detecting sensor at the second inspection station.

10. The method according to claim 8 wherein said first radiant energy detecting sensor senses radiant energy from a container in the first portion of the supply of container that is slightly above the rounded heel portion of the container in the first portion of the supply of containers when the container in the first portion of the supply of containers is in its proper upright condition, and the second sensor is positioned to receive thermal energy from a position of a container in the second portion of the supply of containers that is slightly above a rounded heel portion of the container in the second portion of the supply of containers when the container in the second portion of the supply of containers is in its proper upright orientation.

11. Apparatus according to claim 4 wherein:

the first radiant energy detecting sensor is focused to sense thermal energy in a cone of view no greater than 1°; and the second radiant energy detecting sensor is focused to sense thermal energy in a cone of view no greater than 1°.

* * * * *